United States Patent [19]

Buxton et al.

[11] Patent Number: 5,508,044

[45] Date of Patent: Apr. 16, 1996

[54] DILTIAZEM PHARMACEUTICAL SPHEROID FORMULATION

[75] Inventors: Ian R. Buxton; Adrian Brown; Helen Critchley; Stewart T. Leslie; Sandra T. A. Malkowska; Derek A. Prater, all of Cambridge, United Kingdom; Ronald B. Miller, Basel, Switzerland

[73] Assignee: Euro-Celtique, S.A., Luxembourg

[21] Appl. No.: 279,062

[22] Filed: Jul. 22, 1994

Related U.S. Application Data

[63] Continuation of Ser. No. 926,512, Aug. 5, 1992, abandoned.

[30] Foreign Application Priority Data

Aug. 12, 1991 [GB] United Kingdom .................. 9117361

[51] Int. Cl.⁶ ........................................................ A61K 9/16
[52] U.S. Cl. .......................... 424/495; 424/493; 424/479; 424/480; 424/472; 514/869
[58] Field of Search ................................ 424/461, 472, 424/495, 497, 498, 493, 479, 480; 514/869

[56] References Cited

U.S. PATENT DOCUMENTS

| | | | |
|---|---|---|---|
| 4,728,512 | 3/1988 | Mehta et al. | 424/458 |
| 4,891,230 | 1/1990 | Geoghegan et al. | 424/461 |
| 5,156,850 | 10/1992 | Wong et al. | 424/473 |
| 5,286,497 | 2/1994 | Hendrickson et al. | 424/490 |

FOREIGN PATENT DOCUMENTS

| | | |
|---|---|---|
| 3227389 | 10/1989 | Australia . |
| 6798890 | 7/1991 | Australia . |
| 0106443 | 4/1984 | European Pat. Off. . |
| 0288732 | 11/1988 | European Pat. Off. . |
| 0315414 | 5/1989 | European Pat. Off. . |
| 8802253 | 4/1988 | WIPO . |
| 9210097 | 6/1992 | WIPO . |

OTHER PUBLICATIONS

Buris et al. JAMA 3/90 vol. 263 #11, pp. 1507–1512 An Assessment of Dictiazem and Hydrochlorothiazide in Hypertension.

Weinstock Chem Abstracts 117(18) 178319h Antihypertension Compositions Containing Diuretics and Angioprosin II Receptor Antagonists.

"Diuretics Versus Calcium–Channel Blockers in Systemic Hypertension: A Preliminary Multicenter Experience with Hydrochlorothiazide and Sustained–Release Diltiazem", Frishman, et al., American Journal of Cardiology, Dec. 6, 1985, vol. 56, pp. 92H–96H.

"An Assessment of Diltiazem and Hydrochlorothiazide in Hypertension" Buris, et al., JAMA, Mar. 16, 1990, vol. 263 No. 11; pp. 1507–1512.

"A dose escalation trial comparing the combination of diltiazem SR and hydrochlorothiazide with the monotherapies in patients with essential hypertension", Weir, et al. Journal of Human Hypertension (1992) vol. 6 pp. 133–138.

"Comparison of Hydrochlorothiazide and Sustained–Release Diltiaze for Mild–to–Moderate Systemic Hypertension", Frishman, et al, American Journal of Cardiol Mar. 1, 1987, vol. 59, pp. 615–623.

*Primary Examiner*—Thurman K. Page
*Assistant Examiner*—N. Levy
*Attorney, Agent, or Firm*—Steinberg, Raskin & Davidson

[57] ABSTRACT

A solid oral dosage form comprising diltiazem (or a pharmaceutically acceptable salt thereof) in controlled release form and hydrochlorothiazide in immediate release form. Preferably, the controlled release component comprises a plurality of spheroids comprising diltiazem and a spheronizing agent.

2 Claims, No Drawings

5,508,044

DILTIAZEM PHARMACEUTICAL SPHEROID FORMULATION

This is a continuation of application Ser. No. 07/926,512, filed on Aug. 5, 1992, and now abandoned.

BACKGROUND OF THE INVENTION

The present invention relates to a solid oral dosage form and to a process for its preparation. In particular it relates to a solid oral dosage form comprising a combination of diltiazem and hydrochlorothiazide for the treatment of hypertension.

Thiazide diuretics, and in particular hydrochlorothiazide, are widely used in antihypertensive therapy. Diltiazem is a calcium antagonist which has been shown to be useful in treating chronic heart disease such as angina and hypertension. The administration of diltiazem together with hydrochlorothiazide has been reported to produce significant additive effects in mild to moderate hypertension with twice-daily dosing (see Burris et al, JAMA, 263, (11), 1507–12, 1990).

OBJECTS AND SUMMARY OF THE INVENTION

It is an object of the present invention to provide a combined dosage form comprising diltiazem and hydrochlorothiazide suitable for once daily administration for the treatment of hypertension.

The present invention therefore provides a solid oral dosage form comprising diltiazem or a pharmaceutically acceptable salt thereof in controlled release form and hydrochlorothiazide in immediate release form.

DETAILED DESCRIPTION

Suitable pharmaceutically acceptable salts of diltiazem for use according to the present invention include pharmaceutically acceptable acid addition salts. The hydrochloride salt is particularly preferred.

The dosage forms according to the invention utilize diltiazem or its pharmaceutically acceptable salts in controlled release form. Known controlled release systems which may be used according to the invention include diffusion, erosion or osmosis controlled delivery systems. Dissolution may be through a rate-controlling barrier or from a matrix system. Controlled release matrices containing swellable polymers which are capable of modifying the diffusion of the active ingredient across the barrier have also been described, and may be utilized in the present invention.

Erosion-controlled release systems deliver the active ingredient by slow dissolution or breakup up of the matrix. Suitable adjuvants such as hydrophilic gel-forming adjuvants or hydrophobic adjuvants may be added. In a hydrophilic matrix, the release of the active ingredient will be controlled by the gel layer formed on contact with water or digestive fluids. Where hydrophobic adjuvants are employed, it is their erosion which controls the release rate.

In osmotic systems delivery of the active ingredient is controlled by the permeability of the membrane and the osmotic pressure generated by core matrix.

Alternatively release of the active ingredient may also be pH or time controlled.

Suitable materials for inclusion in a controlled release matrix include, for example (a) Hydrophilic or hydrophobic polymers, such as gums, cellulose esters, cellulose ethers, protein derived materials, nylon, acrylic resins, polylactic acid, polyvinylchloride, starches, polyvinylpyrrolidones, cellulose acetate phthalate. Of these polymers, cellulose ethers, especially substituted cellulose ethers such as alkylcelluloses and acrylic resins (for example methacrylates such as methacrylic acid copolymers), are preferred. The controlled release matrix may conveniently contain between 1% and 80% (by weight) of the hydrophilic or hydrophobic polymer.

(b) Digestible, long chain ($C_8$–$C_{50}$, especially $C_8$–$C_{40}$), substituted or unsubstituted hydrocarbons, such as fatty acids, hydrogenated vegetable oils such as Cutina™, fatty alcohols, glyceryl esters of fatty acids, for example, glyceryl monostearate mineral oils and waxes (such as beeswax, glycowax, castor wax or carnauba wax). Hydrocarbons having a melting point of between 25° C. and 90° C. are preferred. Of these, long chain hydrocarbon materials, fatty (aliphatic) alcohols are preferred. The matrix may contain up to 60% (by weight) of at least one digestible, long chain hydrocarbon.

(c) Polyalkylene glycols. The matrix may contain up to 60% (by weight) of at least one polyalkylene glycol.

A suitable matrix comprises one or more cellulose ethers or acrylic resins, one or more $C_{12}$–$C_{36}$, preferably $C_{14}$–$C_{22}$, aliphatic alcohols and/or one or more hydrogenated vegetable oils.

A particularly suitable matrix comprises one or more alkylcelluloses, one or more $C_{12}$–$C_{36}$, preferably $C_{14}$–$C_{22}$, aliphatic alcohols and optionally one or more polyalkylene glycols.

The cellulose ether is preferably a substituted cellulose ether such as alkylcellulose and is preferably a substituted alkylcellulose such as ethylcellulose or a hydroxy ($C_1$ to $C_6$) alkyl cellulose, such as hydroxypropylcellulose, hydroxypropylmethylcellulose phthalate and especially hydroxyethylcellulose. Preferably the matrix contains between 2% and 60%, especially between 3% and 50% (by wt) of the cellulose ether).

The acrylic resin is preferably a methacrylate such as methacrylic acid copolymer USNF Type A (Eudragit L™), Type B (Eudragit S™), Type C (Eudragit L 100-55™), Eudragit NE 30D, Eudragit E, Eudragit RL and Eudragit RS. Preferably the matrix contain between 2% and 60% by weight, particularly between 3% and 50% by weight of the acrylic resin.

The aliphatic alcohol may be, for example, lauryl alcohol, myristyl alcohol or stearyl alcohol but is preferably cetyl alcohol or cetostearyl alcohol. The amount of the aliphatic alcohol or hydrogenated vegetable oil will be determined by the precise rate of diltiazem release required and also on whether the polyalkylene glycol is present or absent. In the absence of polyalkylene glycol, the matrix preferably contains between 8% and 40%, especially between 12% and 36% (by wt) of the aliphatic alcohol. When polyalkylene glycol is present in the oral dosage form then the combined weight of the aliphatic alcohol and the polyalkylene glycol preferably constitutes between 2% and 40%, especially between 8% and 36% (by wt) of the matrix.

The polyalkylene glycol may be, for example, polypropylene glycol or, which is preferred, polyethylene glycol. The number average molecular weight of the at least one polyalkylene glycol is preferably between 200 and 1500 especially between 400 and 12000.

In addition to the above ingredients, the controlled release matrix may also contain suitable quantities of other materials, e.g. diluents, lubricants, binders, granulating aids, colorants, surfactants, anti-adherents, flavorants and glidants that are conventional in the pharmaceutical art.

The diltiazem containing controlled release matrix of the invention can readily be prepared by dispersing the active ingredient in the controlled release system using conventional pharmaceutical techniques such as wet granulation, dry blending, dry granulation or coprecipitation.

In a preferred embodiment of the present invention the controlled release component comprises a plurality of beads, the beads comprising diltiazem or a pharmaceutically acceptable salt thereof and optionally a bead forming agent.

The term "bead" is conventional in the pharmaceutical art and means a spherical granule having a diameter of between 0.1 mm and 2.5 mm, especially between 0.5 mm and 2 mm. Included within this are inert cores composed of excipients which are coated with the active ingredient. Suitable inert excipients include sucrose, starch and microcrystalline celluloses. Preferably, however, the bead comprises spheroids comprising the active ingredient and optionally a spheronizing agent.

The beads preferably contain between 40% and 98%, more preferably between 60% and 85%, especially between 70% and 85% by weight of diltiazem or its pharmaceutically acceptable salts.

In a particularly preferred embodiment of the invention the controlled release component comprises a plurality of spheroids comprising diltiazem or a pharmaceutically acceptable salt thereof and a spheronizing agent.

The spheronizing agent may suitably be any pharmaceutically acceptable material which may be spheronized together with the active ingredient to form spheroid cores. A preferred spheronizing agent is microcrystalline cellulose. The microcrystalline cellulose employed may be, for example, Avicel PH 101 or Avicel PH 102 (™, FMC Corporation) Preferably, the spheronizing agent, when present, is present in an amount from about 1% to about 60%, preferably from about 15% to about 40% by weight of the spheroid core.

In addition the spheroids may also contain a binder. Suitable binders which may be used are well known in the art and include hydrophilic polymers of hydrocolloids such as cellulose polymers, especially cellulose ethers, acrylic resins and gums. Water soluble hydroxy lower alkyl celluloses such as hydroxypropylcellulose are preferred. The binder is preferably present in an amount of from 1% to 40% by weight of the spheroid core.

Optionally the spheroid core may also contain other pharmaceutically acceptable excipients and diluents which facilitate spheronization such as sugars (for example sucrose, dextrose, maltose or lactose) or sugar alcohols (for example mannitol, xylitol or sorbitol). Colorants may also be included in the spheroid core.

The spheroid cores are preferably film coated with a material which permits release of the diltiazem at a controlled rate in an aqueous medium. Suitable film coating materials include water insoluble waxes and polymers such as polymethacrylates (for example Eudragit polymers™) or preferably water insoluble celluloses particularly ethylcellulose. This film coat may also include water soluble polymers such as polyvinylpyrrolidone or preferably a water soluble cellulose such as hydroxypropylmethylcellulose and hydroxypropylcellulose. It will be appreciated that the ratio of water insoluble to water soluble material will depend on the release rate required and the solubility of the materials selected. The ratio of water soluble polymer to water insoluble polymer is preferably 1:20 to 1:2.

The controlled release coating preferably includes one or more plasticizers conventional in the art such as diethylphthalate but particularly dibutyl sebacate; surfactants such as sorbitan trioleate, sorbitan monolaurate or preferably polysorbate 80 (Tween 80™) and tack-modifiers such as talc or preferably colloidal anhydrous silica.

The amount of plasticizer, when present, will depend on the particular plasticizer selected. In general, the plasticizer is present in an amount of from about 1% to about 25% by weight of the controlled release film coat.

The surfactant, when present, is suitably present in an amount of from about 1% to about 25% by weight of the controlled release film coat.

The tack-modifier, when present, is also suitably present in an amount of from about 1% to about 25% by weight of the controlled release film coat.

A preferred controlled release film coating comprises from about 50% to about 95% ethylcellulose, from about 5% to about 15% colloidal anhydrous silica, from about 5% to about 15% dibutyl sebacate, and from about 5% to about 15% polysorbate 80 (Tween 80™).

The controlled release film coating layer can be formed on the surface of the diltiazem containing spheroid core using conventional coating methods, for example, fluidized bed or pan coating. The coating materials may be applied as a solution or suspension. Suitable solvent systems include water, dichloromethane, ethanol, methanol, isopropyl alcohol and acetone or a mixture thereof. The coating solution or suspension preferably contains from about 2% to about 60%, preferably from about 2% to about 20% by weight of coating materials.

The amount of controlled release coating material will depend on the desired release rate but is generally in the range of from about 1% to about 25%, preferably from about 2% to about 8% by weight of the controlled release coated spheroid.

The diltiazem containing spheroids according to the invention may be prepared by (a) granulating a mixture comprising diltiazem or a pharmaceutically acceptable salt thereof, water and optionally spheronizing agent;

(b) extruding the granulated mixture to give an extrudate;

(c) spheronizing the extrudate until spheroid cores are formed;

(d) drying the spheroid cores; and, optionally, (e) film coating the spheroid cores.

The solid oral dosage form according to the invention may be formulated as a bilayer tablet. In a preferred embodiment, however, the solid oral dosage form comprises a core comprising diltiazem or a pharmaceutically acceptable salt thereof in controlled release form and an outer coating layer comprising hydrochlorothiazide for immediate release.

Preferably, the hydrochlorothiazide outer coating layer includes a water soluble hydrophilic polymer such as cellulose ether (for example hydroxypropylcellulose or hydroxypropylmethyl cellulose), polyvinylpyrrolidone or xanthan gum. The ratio of polymer to hydrochlorothiazide is preferably from 10:1 to 1:10. Other coating excipients such as plasticizers, surfactants, tack modifiers, opacifiers and colorants may also be present. The hydrochlorothiazide and excipients are preferably present in the ratio of from about 10:1 to about 1:10.

The hydrochlorothiazide-containing outer coating layer can be formed on the diltiazem-containing controlled release spheroid using conventional coating techniques such as fluidised bed coating or pan coating. Suitable solvents for the coating solution include water, ethanol, methanol, isopropanol or dichloromethane. It will be appreciated that the amount of coating material in the coating solution will depend on the ratio of drug to polymer and the viscosity of the solution. Conveniently the coating solution contains from about 1% to about 60% by weight of coating materials.

The weight ratio of diltiazem to hydrochlorothiazide in the dosage forms according to the invention typically ranges from about 30:1 to about 4:1, preferably from about 20:1 to about 6:1. The dosage form according to the present invention may suitably be administered once or twice daily. Conveniently for once-daily administration, the dosage form contains 120 mg to 480 mg of diltiazem or a pharmaceutically acceptable salt thereof, preferably diltiazem hydrochloride, and 6.25 mg to 25 mg hydrochlorothiazide. A preferred dosage form according to the invention for once daily administration contains 150 mg diltiazem hydrochloride and 12.5 mg hydrochlorothiazide.

For twice daily administration the dosage form conveniently contains 60 mg to 240 mg of diltiazem or a pharmaceutically acceptable salt thereof, preferably diltiazem hydrochloride, and 3.125 mg to 12.5 mg hydrochlorothiazide. A preferred dosage form for twice daily administration contains 75 mg diltiazem hydrochloride and 6.25 mg hydrochlorothiazide.

Compositions according to the invention may be filled into capsules or sachets or compressed into tablets using conventional pharmaceutical techniques.

When the dosage form of the invention is administered orally the hydrochlorothiazide incorporated in the outer coating layer is rapidly released. The release and dissolution rate of the diltiazem in the core is controlled. When administered the dosage form provides rapid diuresis due to the fast release of the hydrochlorothiazide but also maintains an antihypertensive effect over a prolonged period of time because of the controlled release of diltiazem from the core.

DETAILED DESCRIPTION OF THE PREFERRED EMBODIMENTS

The following examples illustrate various aspects of the present invention. They are not to be construed to limit the claims in any manner whatsoever.

EXAMPLE 1

In example 1, capsules made in accordance with the present invention were prepared as follows.

First, diltiazem spheroid cores were prepared by blending the diltiazem and microcrystalline cellulose using a high shear mixer. The mixer was wet granulated, and extruded to give an extrudate which was spheronized and dried in a fluid bed drier. The spheroids were sieved to give a particle size of 0.85 to 1.7 mm.

The controlled release film coating was prepared by dispersing the ingredients in a dichloromethane/methanol solvent system and applying the film coating to the diltiazem spheroid cores in a fluid bed coater. The resulting film coated spheroids were sieved.

Further information concerning the diltiazem spheroid cores and the controlled release film coating is provided in Tables 1 and 2, respectively.

TABLE 1

Diltiazem Spheroid Cores

| Material | mg |
| --- | --- |
| Diltiazem hydrochloride U.S.P. | 150 |
| Microcrystalline cellulose E.P. (Avicel PH101) | 37.5 |
| Purified water E.P. | q.s. |
| Total | 187.5 |

TABLE 2

Controlled Release Film Coat

| Material | mg |
| --- | --- |
| Diltiazem hydrochloride spheroid core | 187.5 |
| Ethylcellulose N10 U.S.N.F. | 9.225 |
| Colloidal anhydrous silica E.P. (Aerosil 130) | 1.235 |
| Dibutyl sebacate U.S.N.F. | 0.928 |
| Polysorbate 80 E.P. (Tween 80) | 0.989 |
| Dichloromethane BS 1994 | q.s. |
| Methanol B.P. 1973 | q.s. |
| Total | 200 |

A dispersion of hydrochlorothiazide and hydroxypropylmethylcellulose was prepared according to the formula set forth in Table 3 below. The diltiazem-containing controlled release spheroids were then film coated with the dispersion of hydrochlorothiazide and hydroxypropylmethylcellulose in a fluid bed coater.

TABLE 3

Hydrochlorothiazide Film Coat

| Material | mg |
| --- | --- |
| Diltiazem hydrochloride controlled release film coated spheroids | 200 |
| Hydrochlorothiazide E.P. | 12.5 |
| Hydroxypropylmethylcellulose 5 cps E.P. (Methocel E5) | 2.5 |
| Purified water E.P. | q.s. |
| Total | 215 |

The resulting tablets were thereafter subjected to dissolution testing measured by EP basket apparatus at 100 rpm in a pH 4.5 EP phosphate buffer. The results obtained are recorded in Table 4 below:

TABLE 4

Hydrochlorothiazide Dissolution

| Time | Percent |
| --- | --- |
| 10 minutes | 100% |

Diltiazem Dissolution

| Time (hours) | Diltiazem controlled release/ hydrochlorothiazide spheroid (%) |
| --- | --- |
| 1 | 8 |
| 2 | 20 |
| 3 | 32 |
| 4 | 41 |
| 5 | 50 |
| 6 | 57 |
| 8 | 66 |

TABLE 4-continued

| 10 | 73 |
| 11 | 77 |
| 15 | 83 |

The diltiazem release rate was unchanged by the application of the hydrochlorothiazide layer.

EXAMPLES 2–3

In Example 2, a controlled release diltiazem core having the formulation set forth in Table 6 below was prepared.

TABLE 6

Diltiazem Cores

| Material | | mg |
|---|---|---|
| Diltiazem hydrochloride | Jap.P. | 120.0 |
| Lactose | E.P. | — |
| Hydroxyethylcellulose | E.P. | 45.0 |
| Povidone K25 | B.P. | 10.0 |
| Purified water | E.P. | N.D. |
| Cetostearyl alcohol | B.P. | 30.0 |
| Purified talc | E.P. | 6.0 |
| Magnesium stearate | E.P. | 6.0 |
| Total Weight (mg) | | 217.0 |

In Example 3, a controlled release diltiazem core having the formulation set forth in Table 7 below was prepared.

TABLE 7

Diltiazem Cores

| Material | | mg |
|---|---|---|
| Diltiazem hydrochloride | Jap.P. | 120.0 |
| Microcrystalline cellulose | E.P. | 44.5 |
| Colloidal anhydrous silica | E.P. | 20.0 |
| Eudragit NE40D | | 80.0* |
| Cetostearyl alcohol | B.P. | 52.5 |
| Magnesium stearate | E.P. | 3.0 |
| Total Weight (mg) | | 320.0 |

*mg solids

The diltiazem-containing controlled release cores of Examples 2 and 3 may be film coated with hydrochlorothiazide according to the procedure described in Example 1.

The examples provided above are not meant to be exclusive. Many other variations of the present invention would be obvious to those skilled in the art, and are contemplated to be within the scope of the appended claims.

What is claimed is:

1. A solid oral dosage form for the treatment of hypertension in humans, comprising a core comprising a plurality of spheroids comprising diltiazem or pharmaceutically acceptable salt thereof, and a spheronizing agent, wherein said diltiazem or pharmaceutically acceptable salt thereof is present in an amount effective to render an antihypertensive effect, said core including a water-insoluble material selected from the group consisting of a wax, an alkylcellulose and a polymethacrylate in an amount effective to prolong the release of said diltiazem over a desired period of time when said dosage form is contacted with water or digestive fluids, wherein said spheroids are coated with a controlled release film coating comprising from about 50% to about 95% ethylcellulose, from about 5% to about 15% dibutyl sebacate, and from about 5% to about 15% polysorbate 80; and an immediate release coating on said core including an effective amount of hydrochlorothiazide to render a diuretic effect when said dosage form is contacted with water or digestive fluids.

2. A solid oral dosage form for the treatment of hypertension in humans, comprising a plurality of beads comprising diltiazem or a pharmaceutically acceptable salt thereof in an amount effective to render an antihypertensive effect, and a controlled release coating in an amount effective to provide a controlled release of said diltiazem or pharmaceutically acceptable salt thereof when said composition is exposed to aqueous solutions, said controlled release coating comprising from about 50% to about 95% water insoluble material selected from the group consisting of a wax, an alkylcellulose and a polymethacrylate, from about 1% to about 25% plasticizer, from about 1% to about 25% surfactant, and from about 1% to about tack-modifier; and an immediate release outer coating comprising effective amount of hydrochlorothiazide to render a diuretic effect, the weight ratio of diltiazem or its pharmaceutically acceptable salt to hydrochlorothiazide being from about 30:1 to about 4:1.

* * * * *

UNITED STATES PATENT AND TRADEMARK OFFICE
CERTIFICATE OF CORRECTION

PATENT NO. : 5,508,044

DATED : April 16, 1996

INVENTOR(S) : Ian R. BUXTON, et al.

It is certified that error appears in the above-indentified patent and that said Letters Patent is hereby corrected as shown below:

Col. 8, line 42, after "about", insert --25%--.

Signed and Sealed this

Eighth Day of October, 1996

Attest:

BRUCE LEHMAN

*Attesting Officer*           *Commissioner of Patents and Trademarks*